United States Patent [19]
Collica et al.

[11] 3,984,696
[45] Oct. 5, 1976

[54] RADIATION GUARD FOR X-RAY TABLE

[75] Inventors: Carl Collica, New Rochelle; Leonard Epifano, Rye; Ralph Farella, Scarsdale, all of N.Y.

[73] Assignee: Medi-Ray, Inc., Tuckahoe, N.Y.

[22] Filed: Dec. 11, 1974

[21] Appl. No.: 531,526

[52] U.S. Cl. ............................................. 250/519
[51] Int. Cl.² ........................................ G21F 3/02
[58] Field of Search ..................... 250/452, 515, 519

[56] References Cited
UNITED STATES PATENTS

| | | | |
|---|---|---|---|
| 2,718,598 | 9/1955 | Graf | 250/519 X |
| 2,794,128 | 5/1957 | Shasky | 250/519 |
| 3,286,094 | 11/1966 | Pretto | 250/519 |

*Primary Examiner*—Davis L. Willis
*Attorney, Agent, or Firm*—Martin Novack

[57] ABSTRACT

A radiation guard suitable for use in conjunction with a diagnostic table and penetrable by the hands of an operator to facilitate moving or examining a patient positioned on a table. In accordance with the invention there is provided a supportive frame mountable at about an edge of the table so as to extend vertically from about the edge, the frame comprising at least a pair of spaced bars. A plurality of strips of flexible radiation shielding material are mounted across the bars in closely spaced relationship, the strips being mounted sufficiently close together to prevent substantial radiation leakage through the frame. The hands of an operator can be inserted between the adjacent strips to manually reposition or examine a patient while protecting most of the operator's body from substantial radiation.

9 Claims, 4 Drawing Figures

RADIATION GUARD FOR X-RAY TABLE

BACKGROUND OF THE INVENTION

This invention relates to radiation shielding apparatus and, more particularly, to a radiation guard especially suitable for use in conjunction with a diagnostic table, such as an X-ray table.

There is a well recognized need to protect medical personnel from extended exposure to radiation, such as X-rays, or to patients that have received radioactive materials for therapy, tracing, etc. Ordinarily, the exposure time of a physician, technician or nurse regarding an individual patient will be relatively short and without consequence, but typically a specialist will be subject to possible exposure many times per day. Each patient may be on the equipment for a considerable time with it typically being necessary for medical personnel to manually reposition or examine a patient a number of times. The cumulative effect of exposures during such procedures can be hazardous to medical personnel.

This danger is well understood and, in the hope of minimizing it, it has been suggested that a removable leaded shield could be mounted on the table next to the patient. This is inconvenient, however, since the shield between patient and operator must be removed in order for the operator to manually reposition or examine the patient. To overcome this inconvenience, it has been further suggested that a number of "flaps" of leaded rubber be provided to hang next to an X-ray table, the flaps being readily moved aside by the operator when manual contact with the patient is necessary. This solution is not adequate, however, since the flaps offer no protection when the X-ray table is tilted vertically and, even in the horizontal position, the flaps offer little protection to an operator's body when they have been pushed aside in order to reposition a patient.

It is one object of the present invention to provide a solution to the aforementioned problem.

SUMMARY OF THE INVENTION

The present invention is directed to a radiation guard suitable for use in conjunction with a diagnostic table and penetrable by the hands of an operator to facilitate moving a patient on a table. In accordance with the invention there is provided a supportive frame mountable at about an edge of the table so as to extend vertically from about the edge, the frame comprising at least a pair of spaced bars. A plurality of strips of flexible radiation shielding material are mounted across the bars in closely spaced relationship, the strips being mounted sufficiently close together to prevent substantial radiation leakage through the frame. Thus, the hands of an operator can be inserted between the adjacent strips to manually reposition a patient without exposing the operator to substantial radiation.

In a preferred embodiment of the invention a second frame is foldably mounted on the previously mentioned frame, the second frame being adapted to partially fold to a lateral position, whereby an operator is protected from radiation that might have been scattered above the top of the first-mentioned frame.

Further features and advantages of the invention will become more readily apparent from the following detailed description when taken in conjunction with the accompanying drawings.

DESCRIPTION OF THE PREFERRED EMBODIMENT

Figure 1:
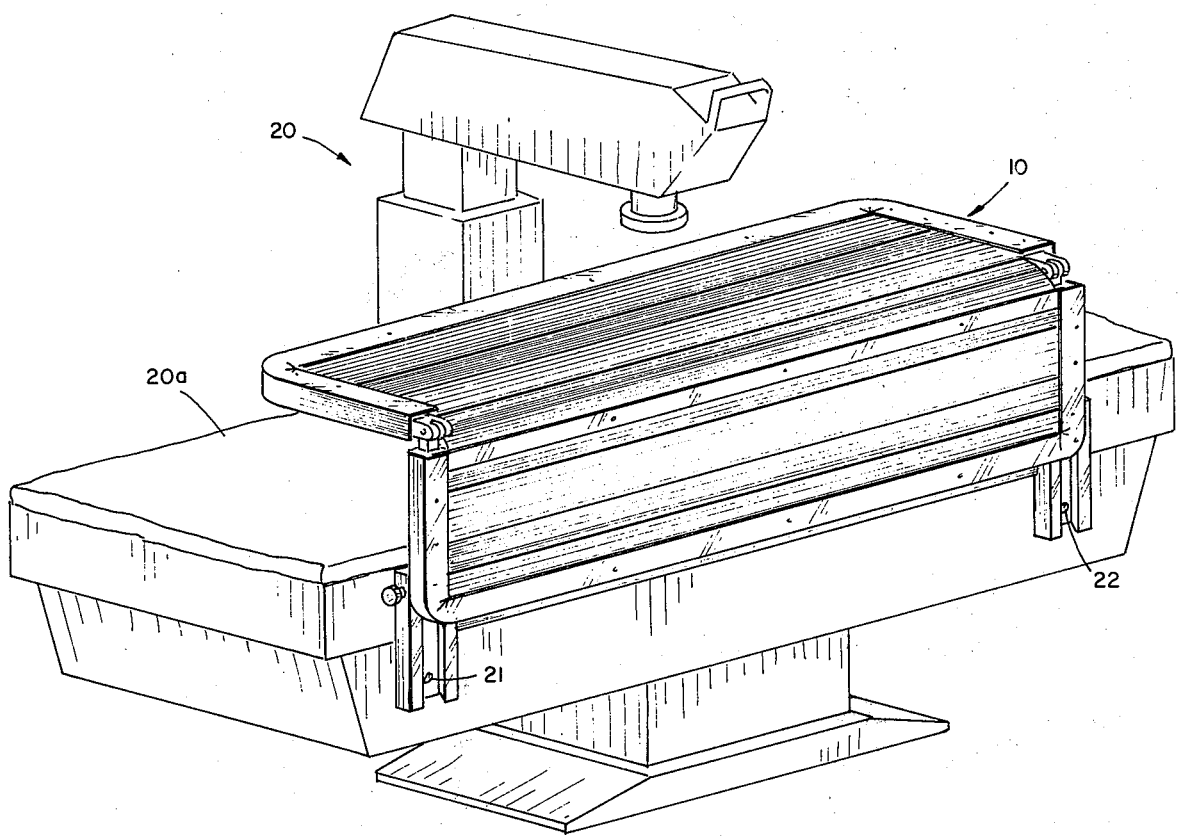
FIG. 1 illustrates an embodiment of the invented radiation guard being used in conjunction with X-ray equipment.

Referring to FIG. 1, there is shown an embodiment of the invented radiation guard 10 being utilized in conjunction with X-ray equipment 20 which includes table 20a. The radiation guard 10, secured to the edge of table 20a by bolt pairs 21 and 22, is capable of providing radiation protection between patient and operator at the "entrance" side of the table and, if desired, above the patient at the entrance side. In the illustration of FIG. 1 the guard 10 is shown in its "fully opened" position which is seen to provide a degree of protection against radiation scattered at an angle above the table as well as side protection.

Figure 2:
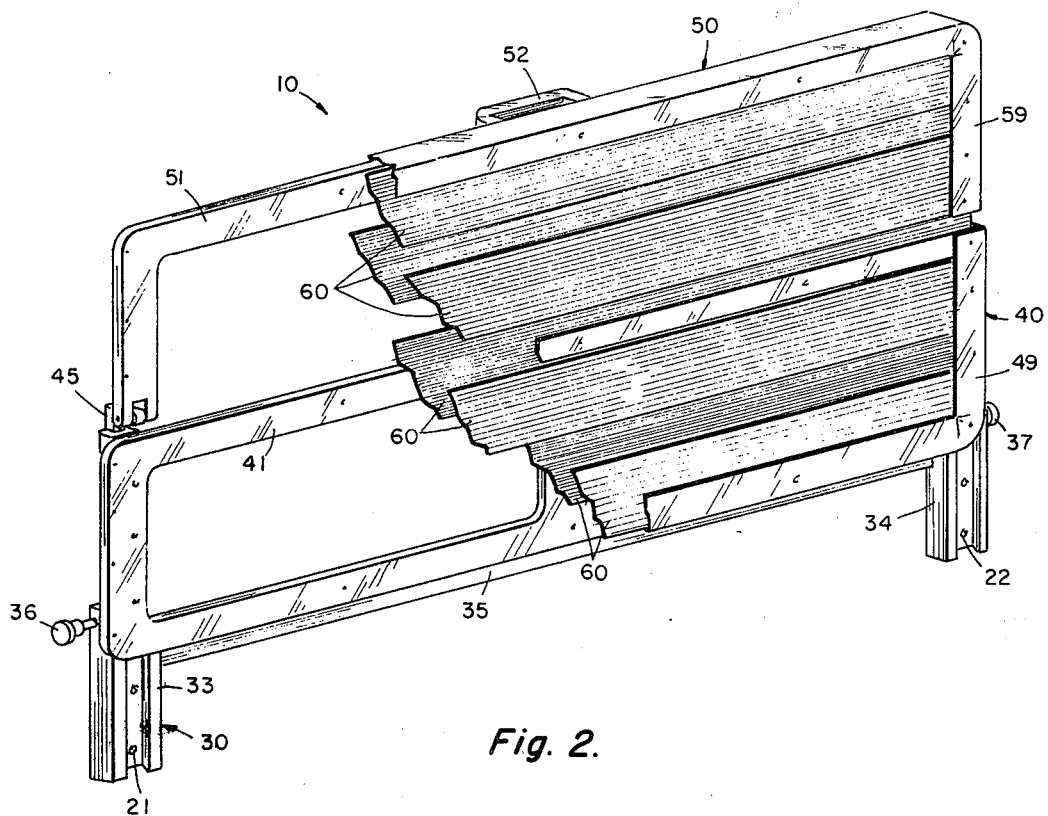
FIG. 2 is a perspective view of the radiation guard in its "half-opened" position.
Figure 3:
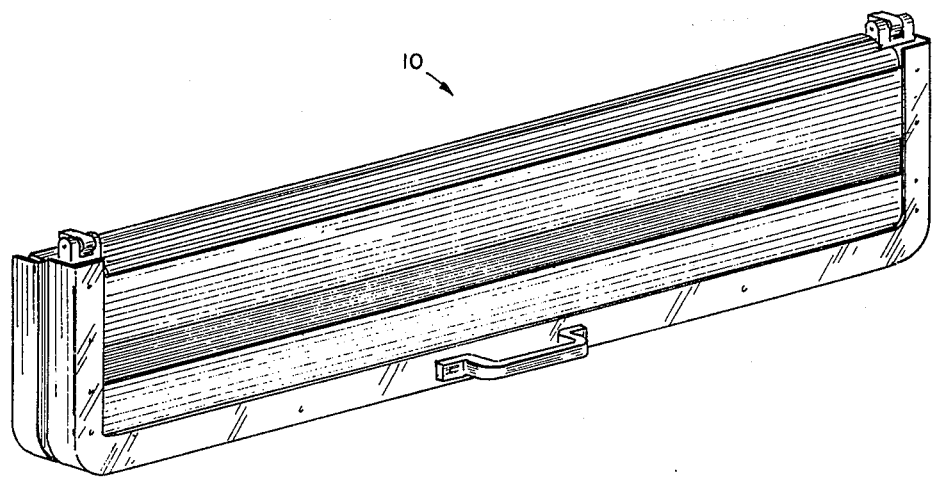
FIG. 3 is a perspective view of the radiation guard in its "closed" position.
Figure 4:
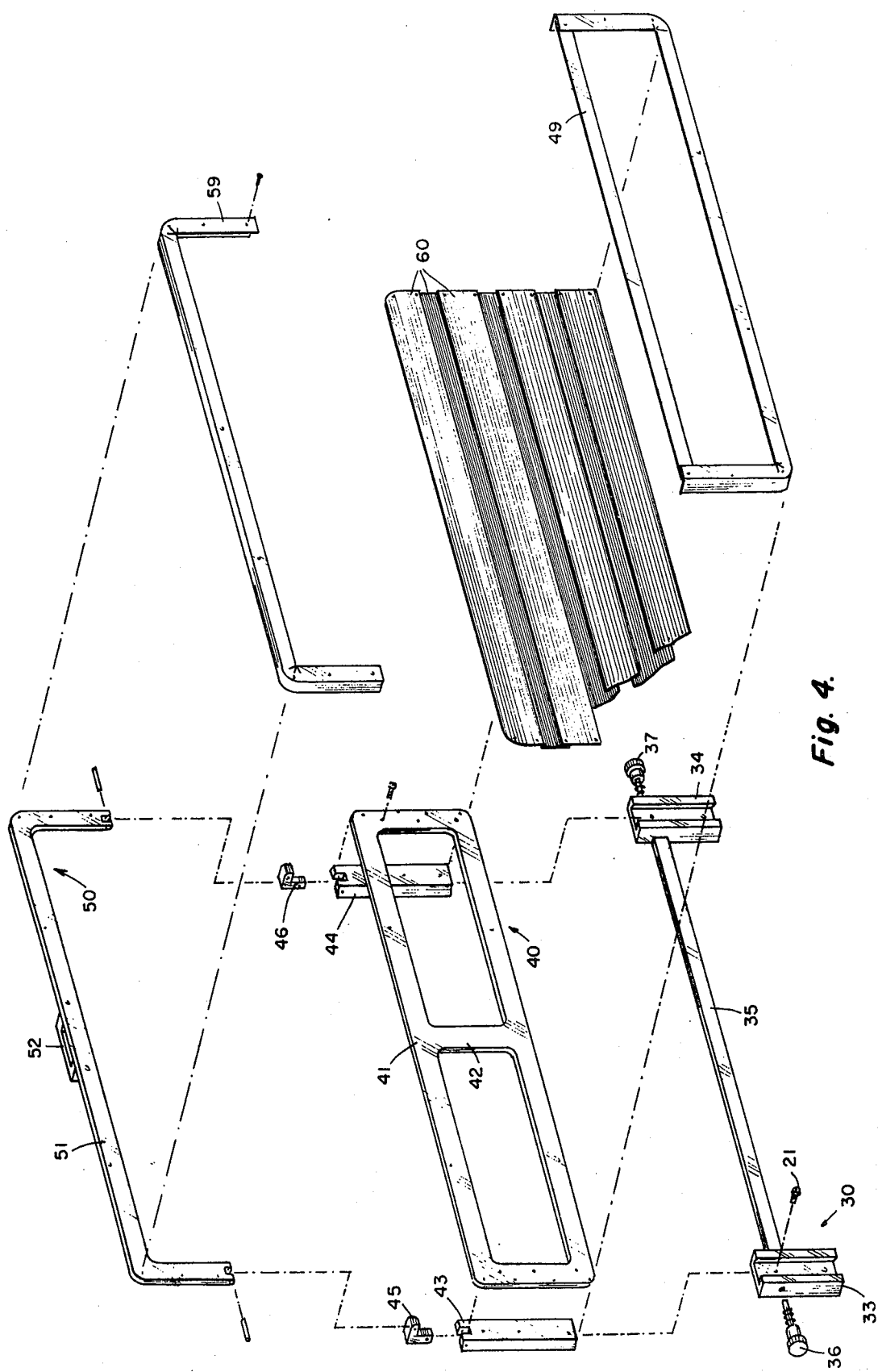
FIG. 4 is an exploded view of the radiation guard.

FIGS. 2 and 3 show the radiation guard 10 in its "half-open" position and folded or "closed" position, respectively, and FIG. 4 shows an exploded view thereof. Referring to the reference numerals of FIGS. 2 and 4, a bracket 30 is securable to a diagnostic table by bolts 21 and 22. The bracket comprises a pair of vertical runners 33 and 34 which are connected by bar 35 and are provided with set screws 36 and 37. A lower frame assembly 40 includes a rectangular metal frame 41 which, in the present embodiment, has a central structural member 42. Mounted on the parallel vertical sides of frame 41 are a pair of bars 43 and 44 of trapazoidal cross-section that are proportioned to slidably fit in the runners 33 and 34 which are similarly shaped. Each of the bars 43 and 44 has an end slot in which an L-shaped hinge mount is secured. These hinge mounts, designated by reference numerals 45 and 46, pivotally support a three-sided metal frame 51, which is the skeleton of an upper frame assembly 50. The upper frame 51 is seen to pivot from a reference slightly forwardly of the bars 43 and 44, so it can swing to the "closed" position (as shown in FIG. 3), while the tops of bars 43 and 44 act as limit stops when the radiation guard is in the "full-open" position (as shown in FIG. 1). A handle 52 is provided for convenient manipulation of the apparatus.

A plurality of strips of lead-rubber 60, i.e., a radiation shielding flexible material such as the type marketed by Bar-Ray Corp., are mounted across the vertical members of frames 41 and 51 by riveting. The strips preferably overlap to a degree which allows an arm to be inserted therebetween, but without this action causing a significant gap between strips. Lower and upper metal trim pieces 49 and 59 conform to the shapes of frames 41 and 51 and are screwed thereto.

When not in use, the radiation guard 10 is in the "closed" position with the bars 43 and 44 at a low level in runners 33 and 34 so that the unit is adjacent the side of table 20. After the patient is on the table, the set screws 36 and 37 are used to hold the unit at a raised level and the half open (FIG. 2) or full open (FIG. 1) position can be employed as desired. The strips are sufficiently flexible to allow the hands and arms of an operator to be inserted therebetween for manipulation of the patient. When the X-ray table is tilted vertically, the radiation guard 10 continues to function in giving the desired protection.

The invention has been described with reference to a specific embodiment, but it will be understood that variations within the spirit and scope of the invention will occur to those skilled in the art. For example, while it is preferred that the lead-rubber strips be mounted horizontally to allow lateral arm motion between strips, it will be recognized that the strips could be mounted vertically. Also, the term diagnostic table is intended generically and not in a limiting sense.

We claim:
1. A radiation guard suitable for use in conjunction with a diagnostic table and penetrable by the hands of an operator to facilitate examining or moving a patient on the table, comprising:
   a supportive frame mountable at about an edge of said table so as to extend normally from said edge, said frame comprising at least one pair of spaced bars; and
   a plurality of strips of flexible radiation shielding material mounted across said bars in closely spaced relationship, said strips being mounted sufficiently close together to prevent substantial radiation leakage through said frame, whereby the hands of an operator can be inserted between adjacent strips to touch a patient without exposing the operator to substantial radiation.

2. A radiation guard as defined by claim 1 wherein adjacent ones of said strips are mounted in overlapping fashion.

3. A radiation guard as defined by claim 2 wherein said pair of spaced bars are normal to said table and said strips are mounted horizontally with respect to said table.

4. A radiation guard as defined by claim 3 wherein said strips comprise lead-rubber.

5. A radiation guard as defined by claim 1 wherein said strips comprise lead-rubber.

6. A radiation guard as defined by claim 1 further comprising a second frame foldably mounted on said first frame and adapted to partially fold to a lateral position over said table and a further plurality of strips of flexible radiation shielding material mounted across said second frame.

7. A radiation guard as defined by claim 6 wherein said second frame is fully foldable in a direction opposite to its partially foldable direction.

8. A radiation guard as defined by claim 7 wherein adjacent ones of said strips are mounted in overlapping fashion.

9. A radiation guard as defined by claim 8 wherein said strips comprise lead-rubber.

* * * * *